(12) United States Patent
Fujii (10) Patent No.: US 9,987,016 B2
(45) Date of Patent: Jun. 5, 2018

(54) LIGATION THREAD FASTENING TOOL AND LIGATION DEVICE

(71) Applicant: OLYMPUS CORPORATION, Tokyo (JP)

(72) Inventor: Yuta Fujii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 99 days.

(21) Appl. No.: 14/062,945

(22) Filed: Oct. 25, 2013

(65) Prior Publication Data

US 2014/0121681 A1    May 1, 2014

Related U.S. Application Data

(60) Provisional application No. 61/721,403, filed on Nov. 1, 2012.

(30) Foreign Application Priority Data

Nov. 1, 2012 (JP) ................... 2012-241856

(51) Int. Cl.
| | |
|---|---|
| *A61B 17/122* | (2006.01) |
| *A61B 17/04* | (2006.01) |
| *A61B 17/06* | (2006.01) |

(52) U.S. Cl.
CPC ........ *A61B 17/122* (2013.01); *A61B 17/0401* (2013.01); *A61B 17/0483* (2013.01); *A61B 17/0487* (2013.01); *A61B 17/06* (2013.01)

(58) Field of Classification Search
CPC .............. A61B 2017/042; A61B 17/04; A61B 17/0487; A61B 17/0483;
(Continued)

(56) References Cited

U.S. PATENT DOCUMENTS

| | | |
|---|---|---|
| 5,879,371 A | 3/1999 | Gardiner et al. |
| 5,902,320 A | 5/1999 | Matsutani et al. |

(Continued)

FOREIGN PATENT DOCUMENTS

| | | |
|---|---|---|
| JP | S58-028610 A | 2/1983 |
| JP | H10-216136 A | 8/1998 |

(Continued)

OTHER PUBLICATIONS

English Abstract only of WO 98/30151 dated Jul. 16, 1998.

*Primary Examiner* — Christopher L Templeton
*Assistant Examiner* — George J Ulsh
(74) *Attorney, Agent, or Firm* — Scully, Scott, Murphy & Presser, P.C.

(57) ABSTRACT

A sufficient gripping force is exerted on a suture thread through an easy process. Provided is a ligation thread fastening tool including: a gripper that has a pair of crimp pieces opposed to each other with a space therebetween and whose inner faces opposed to each other are to be crimped together and that has, between the inner faces, a groove into which a suture thread can be inserted from a first side of the crimp pieces toward a second side thereof; and an accommodation portion that is provided in the gripper from the inner face outward of the groove so as to communicate with the groove and that accommodate an end portion of the suture thread inserted thereinto from the first side through the groove.

10 Claims, 11 Drawing Sheets

(58) Field of Classification Search
CPC .... A61B 2017/0419; A61B 2017/0448; A61B 2017/0454; A61B 2017/0401; A61B 17/122; A61B 17/12
USPC ............... 606/232, 228–231, 233; 24/115 A, 24/129 R, 129 W
See application file for complete search history.

(56) References Cited

U.S. PATENT DOCUMENTS

| | | | |
|---|---|---|---|
| 6,015,428 A * | 1/2000 | Pagedas | A61B 17/0483 606/232 |
| 2006/0293701 A1* | 12/2006 | Ainsworth | A61B 17/0469 606/153 |
| 2012/0089193 A1* | 4/2012 | Stone | A61B 17/0401 606/301 |
| 2012/0165865 A1* | 6/2012 | Fujisaki | A61B 17/0487 606/232 |

FOREIGN PATENT DOCUMENTS

| | | | | |
|---|---|---|---|---|
| JP | 2001-507972 A | | 6/2001 | |
| JP | WO 2013015452 A1 * | | 1/2013 | ......... A61B 17/0401 |

* cited by examiner

LIGATION THREAD FASTENING TOOL AND LIGATION DEVICE

CROSS REFERENCE TO RELATED APPLICATIONS

This application claims the benefit of U.S. Provisional Application No. 61/721,403, filed Nov. 1, 2012, which is hereby incorporated by reference herein in its entirety.

This application claims the benefit of Japanese Patent Application No. 2012-241856, the content of which is incorporated herein by reference.

TECHNICAL FIELD

The present invention relates to a ligation thread fastening tool and a ligation device.

BACKGROUND ART

There are known conventional thread fastening tools used to facilitate an operation for tying a suture thread into a knot, which requires a particularly high degree of skill, in tissue suturing (for example, see PTL 1). The thread fastening tools are configured so as to be able to grip part of a suture thread through an operation that is easier than an operation of tying the suture thread. For example, a thread fastening tool disclosed in PTL 1 is formed of a cylindrical member having a hole into which a suture thread can be inserted, and the thread fastening tool is crimped with the suture thread inserted into the hole, thereby gripping an intermediate position of the suture thread.

CITATION LIST

Patent Literature

{PTL 1} Japanese Translation of PCT International Application, Publication No. 2001-507972

SUMMARY OF INVENTION

Solution to Problem

A first aspect of the present invention is a ligation thread fastening tool including: a gripper that has a pair of crimp pieces opposed to each other with a space therebetween and whose inner faces opposed to each other are to be crimped together and that has, between the inner faces, a groove into which a suture thread can be inserted from a first side of the crimp pieces toward a second side thereof; and an accommodation portion that is provided in the gripper from the inner face outward of the groove so as to communicate with the groove and that accommodate an end portion of the suture thread inserted thereinto from the first side through the groove.

A second aspect of the present invention is a ligation device including: a suture thread; and one of the above-described ligation thread fastening tools attached to one end portion of the suture thread, in which, in the ligation thread fastening tool, the crimp pieces are crimping-fastened to the other end portion of the suture thread inserted into the groove from the first side toward the second side.

DESCRIPTION OF EMBODIMENTS

A ligation thread fastening tool 1 and a ligation device 100 having the same according to one embodiment of the present invention will be described below with reference to the drawings.

Figure 1:
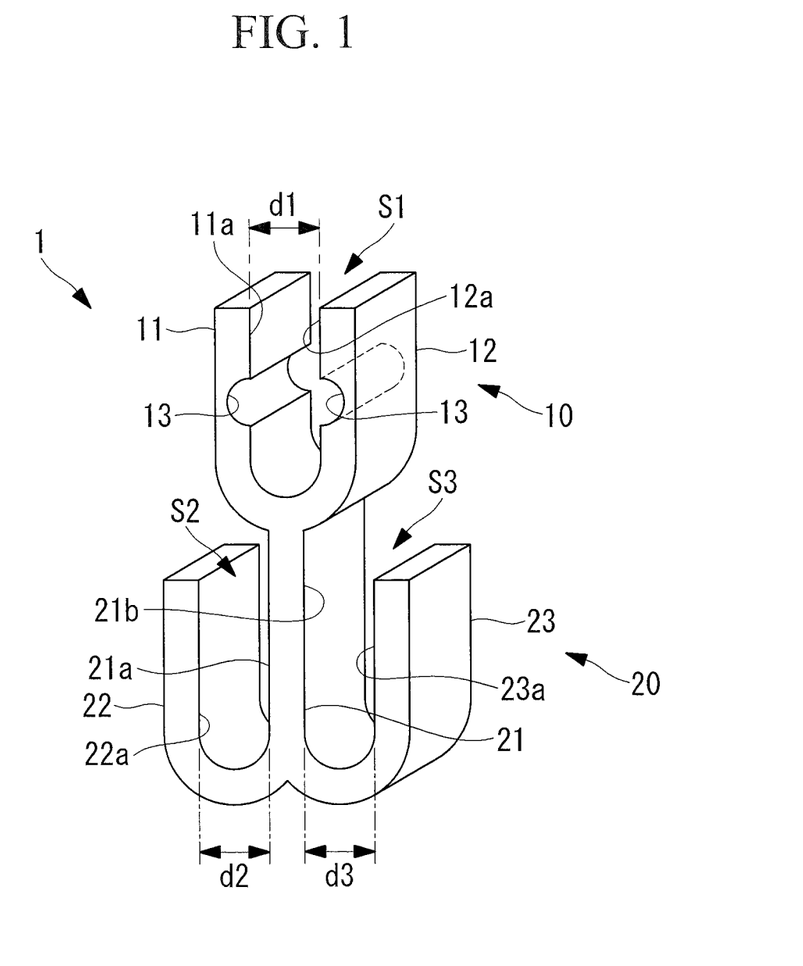
FIG. 1 is a view showing the overall configuration of a ligation thread fastening tool according to one embodiment of the present invention.

The ligation thread fastening tool (hereinafter, simply referred to as "thread fastening tool") 1 according to this embodiment fastens both end portions of a suture thread that is used to suture tissue, and, as shown in FIG. 1, includes a first gripper 10 substantially having a U-shape when viewed from the front and a second gripper 20 substantially having an anchor shape when viewed from the front.

The first gripper 10 has a pair of crimp pieces 11 and 12. The crimp pieces 11 and 12 each have a substantially flat plate shape and are opposed parallel to each other with a distance therebetween. Inner faces 11a and 12a of the crimp pieces 11 and 12 that are opposed to each other are disposed with a distance d1 therebetween, the distance d1 being larger than an outer-diameter dimension of the suture thread. Furthermore, the crimp pieces 11 and 12 are free at a first side and are connected to each other at a second side, which is the opposite side from the first side. Thus, an almost-cuboidal groove S1 into which an end portion of the suture thread can be inserted from the first side toward the second side is formed between the inner faces 11a and 12a of the crimp pieces 11 and 12.

The crimp pieces 11 and 12 each have a concave portion (accommodation portion) 13 that is formed by partially concaving the corresponding inner face 11a or 12a, at an intermediate position thereof between an edge on the first side and an edge on the second side. The concave portion 13 is formed along a direction intersecting the direction connecting the first side and the second side, desirably, as shown in the figure, over the entire length of a width dimension of each of the crimp pieces 11 and 12. A depth dimension of the concave portion 13 (dimension in the thickness direction of each of the crimp pieces 11 and 12) is desirably set to more than half of the outer-diameter dimension of the suture thread.

The second gripper 20 has a shaft piece 21 that is connected to the second side of the crimp pieces 11 and 12 of the first gripper 10 and that is disposed substantially parallel to the crimp pieces 11 and 12, and two crimp pieces 22 and 23 that are opposed to the shaft piece 21 with the shaft piece 21 interposed therebetween. The shaft piece 21 and the two crimp pieces 22 and 23 each have a substantially flat plate shape and are disposed substantially parallel to one another.

As in the crimp pieces 11 and 12 of the first gripper 10, the two crimp pieces 22 and 23 are located so as to have distances d2 and d3, which are each longer than the outer-diameter dimension of the suture thread, between inner faces 22a and 23a thereof and faces 21a and 21b of the shaft piece 21, which are opposed to the inner faces 22a and 23a. Furthermore, the crimp pieces 22 and 23 are free at the first side and are connected to an end of the shaft piece 21 at the second side, which is the opposite side from the first side. Thus, almost-cuboidal grooves S2 and S3 into which the suture thread can be inserted from the first side toward the second side are formed between the face 21a of the shaft piece 21 and the inner face 22a of the crimp piece 22 and between the face 21b of the shaft piece 21 and the inner face 23a of the crimp piece 23.

The first gripper 10 and the second gripper 20 are made of a biocompatible material that is plastically deformed. As the material for the first gripper 10 and the second gripper 20, it is desirable to use stainless steel, especially, SUS316L and SUS316LS having good corrosion resistance and workability. In addition to stainless steel, other metals or resins can be appropriately used. Example metals include: cobalt chrome alloy; pure titanium; titanium alloy, such as β titanium; nickel titanium alloy; and magnesium alloy. Example resins include: bioabsorbable PGA, PLA, PDS, TMC, poly-epsilon-caprolacton, and copolymers thereof; and non-bioabsorbable nylon, polyester, polypropylene, polybutester, and fluorine resin.

Next, the ligation device 100 having the thread fastening tool 1 will be described.

Figure 2:
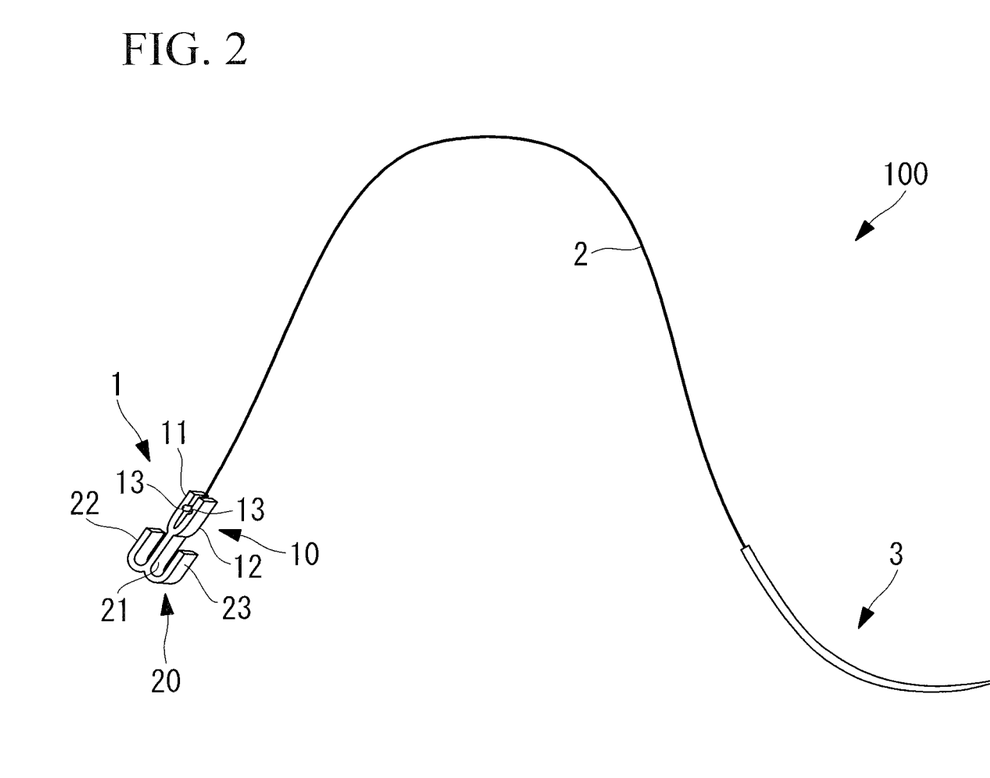
FIG. 2 is a view showing the overall configuration of a ligation device having the ligation thread fastening tool shown in FIG. 1.

As shown in FIG. 2, the ligation device (hereinafter, simply referred to as "device") 100 of this embodiment includes the suture thread 2, the thread fastening tool 1 attached to one end portion of the suture thread 2, and a suture needle 3 attached to the other end portion of the suture thread 2.

The suture thread 2 is desirably made of resin or metal. Furthermore, the suture thread 2 desirably has elasticity so as to keep a straight state. The suture thread 2 may be made of bioabsorbable resin in order to eliminate the need for suture removal.

The suture needle 3 can be appropriately selected by taking account of conditions such as the suture site. Although FIG. 2 shows the suture needle 3 that is curved over the entire length thereof, a suture needle that, for example, is straight or is curved only at a distal end thereof can be used.

Here, a method of attaching the thread fastening tool 1 to one end portion of the suture thread 2 will be described with reference to FIGS. 3A to 3C.

Figure 3A:
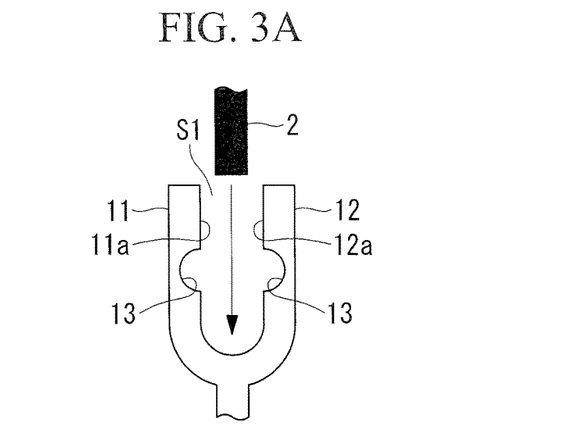
FIG. 3A is a view for explaining how to secure a first gripper of the ligation thread fastening tool shown in FIG. 1 to an end portion of a suture thread.
Figure 3B:
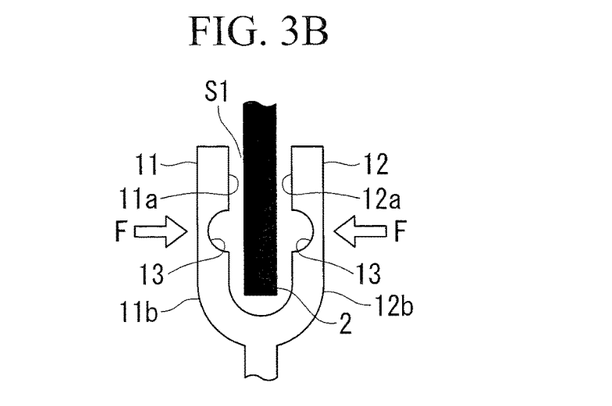
FIG. 3B is a view for explaining how to secure the first gripper of the ligation thread fastening tool shown in FIG. 1 to the end portion of the suture thread.
Figure 3C:
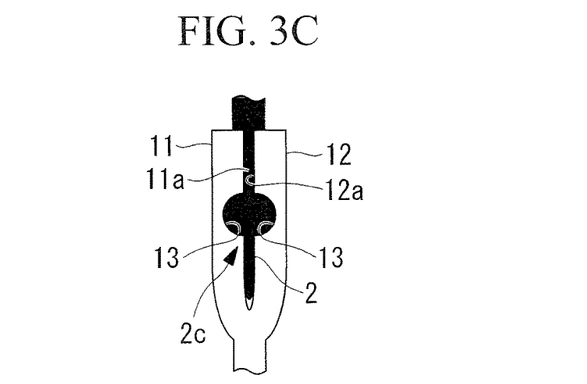
FIG. 3C is a view for explaining how to secure the first gripper of the ligation thread fastening tool shown in FIG. 1 to the end portion of the suture thread.

First, as shown in FIG. 3A, the end portion of the suture thread 2 is inserted into the groove S1 of the first gripper 10 from the first side along the depth direction. Then, as shown in FIG. 3B, the tip of the end portion is placed at a position located after passing the concave portions 13. In this state, pressing forces F are made to act on outer faces 11b and 12b of the pair of crimp pieces 11 and 12 in directions toward each other, as indicated by arrows, to crimp the crimp pieces 11 and 12. Thus, as shown in FIG. 3C, the inner faces 11a and 12a of the crimp pieces 11 and 12 are crimped together, and the end portion of the suture thread 2 sandwiched between the inner faces 11a and 12a is gripped by the first gripper 10.

At this time, even though the inner faces 11a and 12a of the crimp pieces 11 and 12 are crimped together, part of the end portion of the suture thread 2 located at the concave portions 13 retains its outer-diameter dimension without being squeezed by the inner faces 11a and 12a. Specifically, this part of the end portion has an outer-diameter dimension that is larger than the distance between the inner faces 11a and 12a that are crimped together with other parts of the end portion interposed therebetween. With this part of the end portion (hereinafter, also referred to as large-diameter portion 2c), longitudinal movement of the suture thread 2 with respect to the crimp pieces 11 and 12 is locked.

Next, usage of the thus-configured device 100 will be described with reference to FIGS. 4 to 9 by using an example case of wound suturing.

Figure 4:
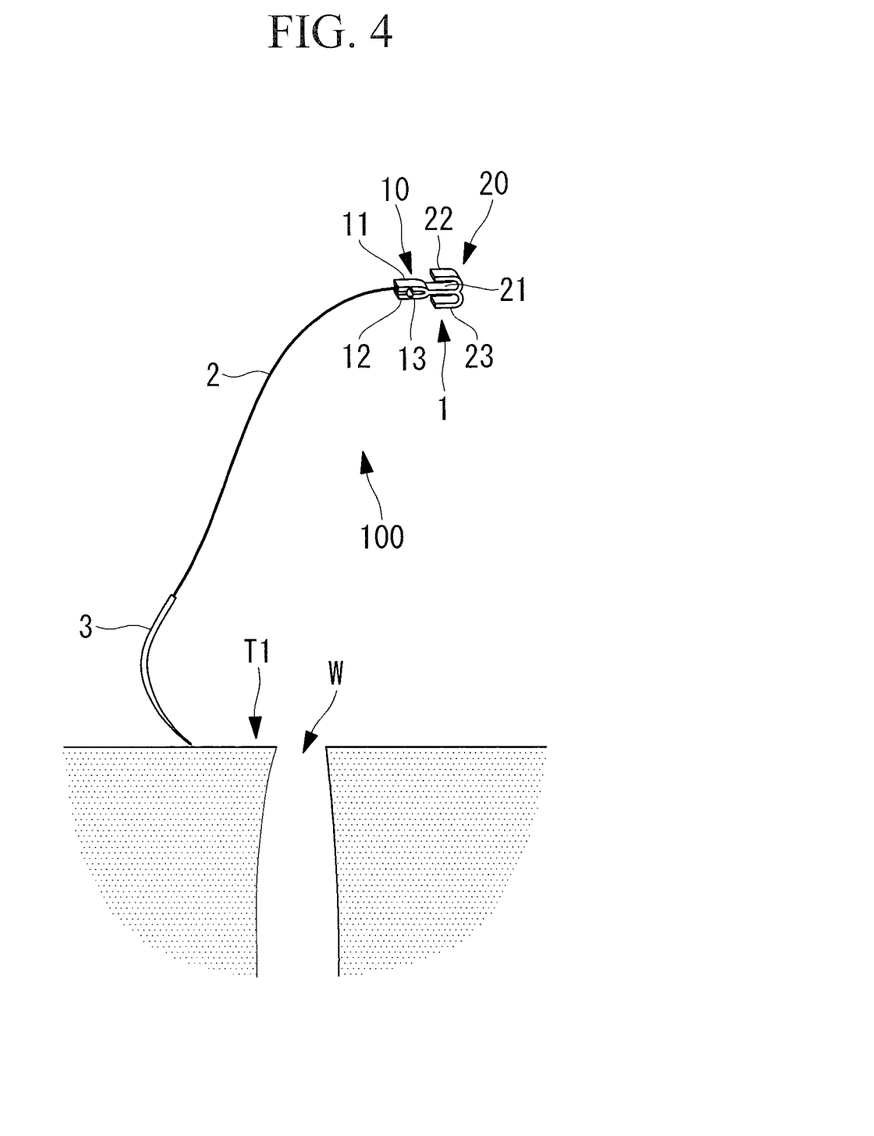
FIG. 4 is a view for explaining the usage of the ligation device shown in FIG. 2.
Figure 5:
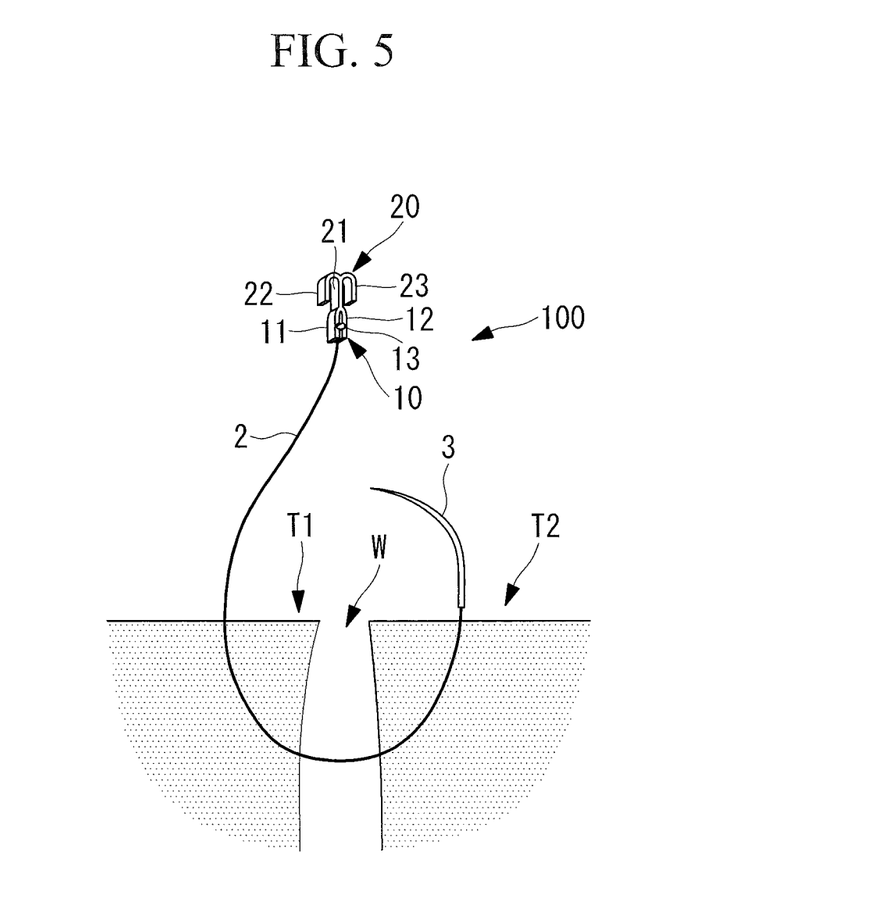
FIG. 5 is a view for explaining the usage of the ligation device shown in FIG. 2.

As shown in FIG. 4, an operator pierces tissue T1 located near a wound W with the suture needle 3 and next, as shown in FIG. 5, pierces tissue T2 facing the tissue T1, with the wound W interposed therebetween, with the suture needle 3, to make the suture thread 2 pass through the tissue T1 and T2.

Figure 6:
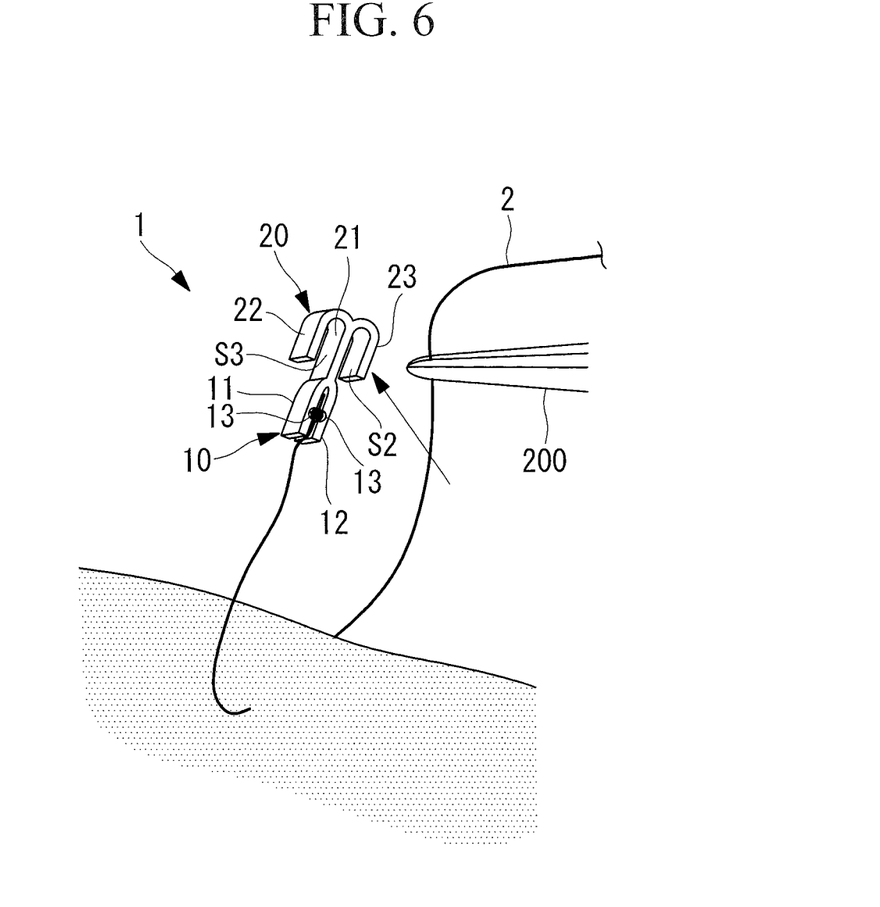
FIG. 6 is a view for explaining the usage of the ligation device shown in FIG. 2.
Figure 7:
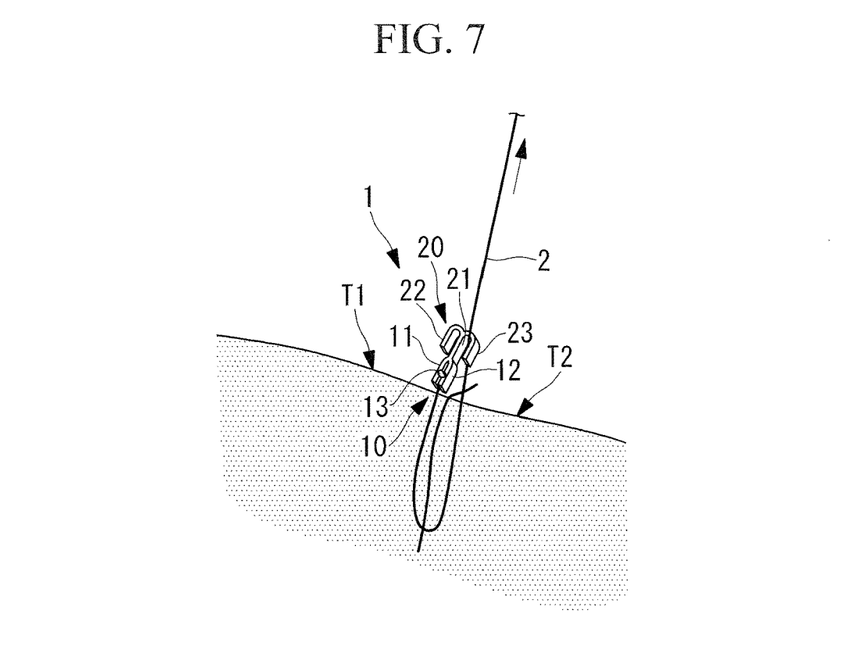
FIG. 7 is a view for explaining the usage of the ligation device shown in FIG. 2.

Next, as shown in FIG. 6, the operator grips the suture thread 2 or the suture needle 3 with forceps 200 etc., and inserts part of the suture thread 2 into one of the two grooves S2 and S3 provided in the second gripper 20 of the thread fastening tool 1. The suture thread 2 may be inserted into both of the grooves S2 and S3. Next, as shown in FIG. 7, the other end portion 2b of the suture thread 2 is pulled in a direction away from the tissue T1 and T2, thereby locating the thread fastening tool 1, connected to the end portion, on the tissue T1 and bringing the tissue T1 and the tissue T2 into close contact with each other.

Here, when the suture thread 2 is pulled, the movement thereof in the pulling direction is locked by the large-diameter portion 2c; therefore, the end portion of the suture thread 2 is prevented from coming out from between the crimp pieces 11 and 12.

Figure 8:
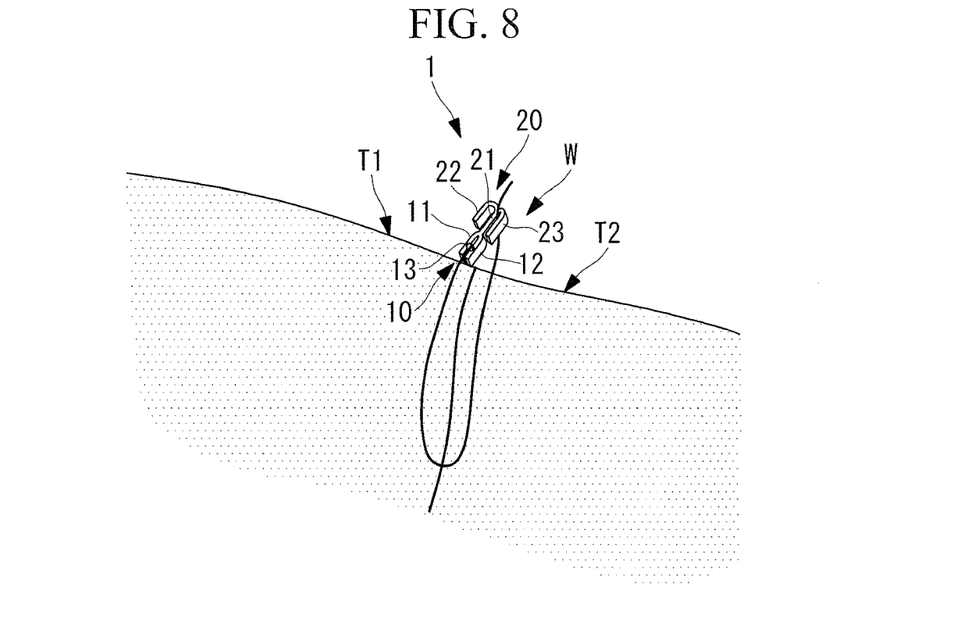
FIG. 8 is a view for explaining the usage of the ligation device shown in FIG. 2.
Figure 9:
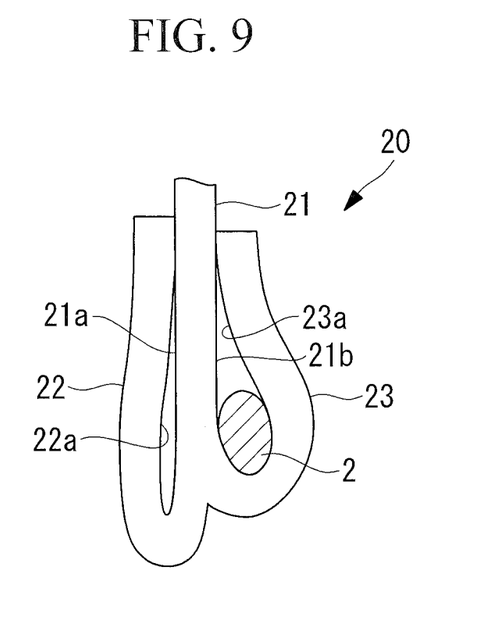
FIG. 9 is a view for explaining a method of securing a second gripper of the ligation thread fastening tool shown in FIG. 1 to the suture thread.

After the suture thread 2 is sufficiently pulled, the operator uses the forceps 200 etc. to grip the crimp pieces 22 and 23 of the second gripper 20 and, as shown in FIG. 9, to crimp the crimp pieces 22 and 23, thereby fastening the second gripper 20 to the suture thread 2. In this way, a portion where the suture thread 2 and the thread fastening tool 1 are fastened functions as a knot in the suture thread 2, and, as shown in FIG. 8, the tissue T1 and the tissue T2 are sutured so as to close the wound W.

In this case, according to this embodiment, the crimp pieces 11 and 12 are crimping-fastened to the suture thread 2 that has been inserted therebetween. Specifically, in order to perform crimping, it is only necessary to apply compressive forces to the flat-plate-shaped crimp pieces 11 and 12 in the thickness directions, thus making it possible to sufficiently crimp the crimp pieces 11 and 12 through an easy process. Thus, a sufficient gripping force of the crimp pieces 11 and 12 with respect to the suture thread 2 is obtained. Furthermore, the movement of the suture thread 2 in the direction in which the suture thread 2 comes out from the first gripper 10 is locked by the large-diameter portion 2c formed in the concave portions 13. As described above, an advantage is afforded in that a sufficient gripping force can be exerted on the suture thread 2 through easy crimping.

Note that, in this embodiment, the first gripper 10 has the crimp pieces 11 and 12 in each of which the concave portion 13 is formed; however, the configurations of the crimp pieces 11 and 12 are not limited thereto, and the concave portion 13 may be formed in just one of the crimp pieces 11 and 12. In this case, the depth direction of the concave portion 13 is appropriately designed such that a space of sufficient size is ensured in the concave portion 13 when the crimp pieces 11 and 12 are crimped together.

Furthermore, in this embodiment, a description has been given of the first gripper 10 in which the concave portions 13 are formed at the intermediate positions in the depth directions of the inner faces 11a and 12a of the crimp pieces 11 and 12; however, the shape of the first gripper 10 is not limited thereto and can be appropriately modified. FIGS. 10A to 14B show modifications of the first gripper 10.

Figure 10A:
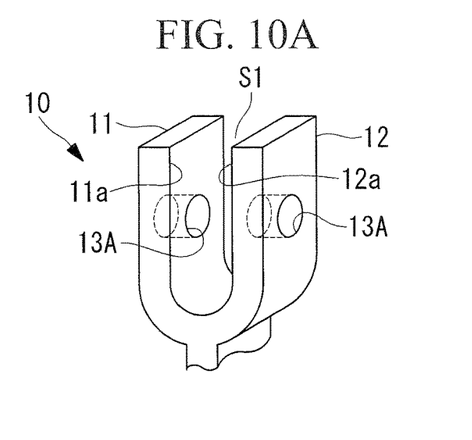
FIG. 10A is a perspective view showing a modification of the first gripper and explaining the usage of the device.

In the first gripper 10 shown in FIG. 10A, through-hole portions (accommodation portions) 13A that pass through the crimp pieces 11 and 12 in the thickness direction are formed in the inner faces 11a and 12a of the crimp pieces 11 and 12. According to this first gripper 10, as shown in FIG. 10B, when the inner faces 11a and 12a are crimped together by crimping the crimp pieces 11 and 12, the large-diameter portion 2c is formed by part of the suture thread 2 located in the through-hole portions 13A.

Figure 10B:
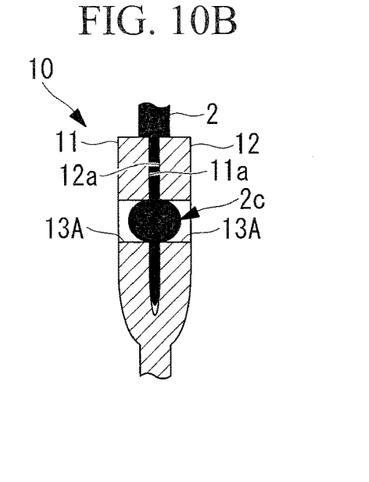
FIG. 10B is a sectional view of the first gripper shown in FIG. 10A.
Figure 10C:
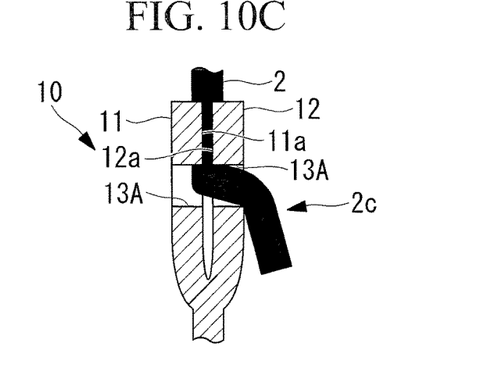
FIG. 10C is a sectional view for explaining another usage of the first gripper shown in FIG. 10A.

FIG. 10C shows another usage of the first gripper 10 shown in FIG. 10A. Specifically, the end portion of the suture thread 2 is made to pass through the through-hole portion 13A so as to be located outside the crimp pieces 11 and 12. By doing so, when the crimp pieces 11 and 12 are crimped, the large-diameter portion 2c is formed by the end portion of the suture thread 2 located outside the through-hole portion 13A and the crimp pieces 11 and 12.

Note that FIGS. 10A to 10C show the configuration of the first gripper 10 of this modification in which the through-hole portion 13A is formed in both of the crimp pieces 11 and 12; however, the configuration of the first gripper 10 of this modification is not limited thereto. For example, it is also possible to adopt a configuration in which the through-hole portion 13A is formed in one of the crimp pieces 11 and 12, and the concave portion 13 is formed in the other. Alternatively, the through-hole portion 13A may be formed in only one of the crimp pieces 11 and 12.

Figure 11A:
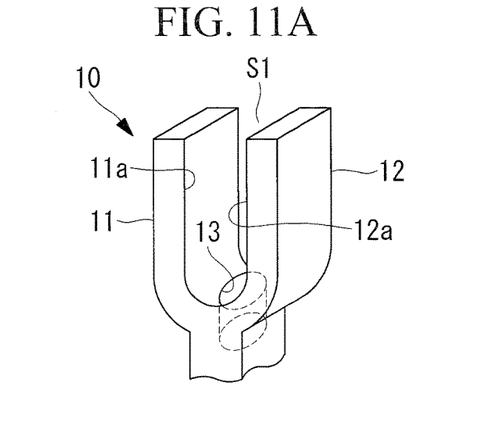
FIG. 11A is a perspective view showing another modification of the first gripper and explaining the usage of the device.
Figure 11B:
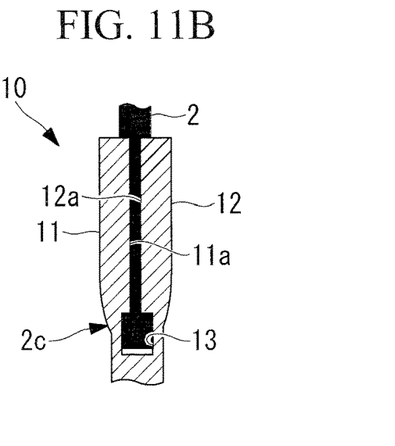
FIG. 11B is a sectional view of the first gripper shown in FIG. 11A.
Figure 12A:
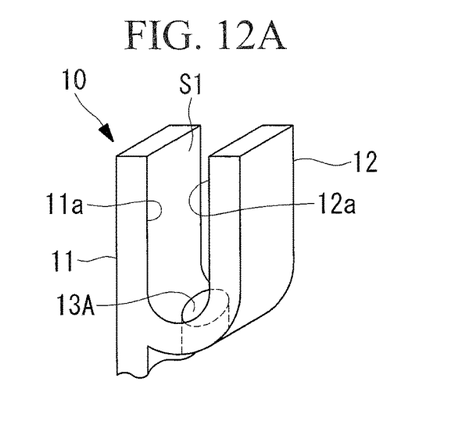
FIG. 12A is a perspective view showing still another modification of the first gripper and explaining the usage of the device.
Figure 12B:
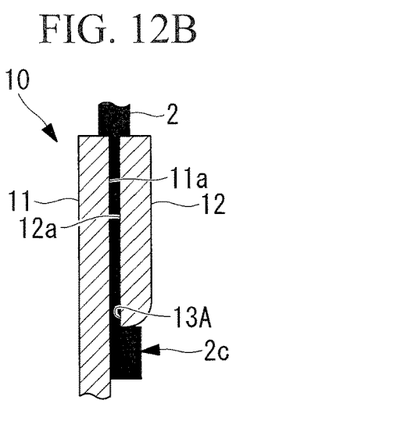
FIG. 12B is a sectional view of the first gripper of FIG. 12A.

In the first gripper 10 shown in FIG. 11A, the concave portion 13 is formed in the bottom of the groove S1. According to this first gripper 10, as shown in FIG. 11B, when the inner faces 11a and 12a are crimped together by crimping the crimp pieces 11 and 12, the large-diameter portion 2c is formed by the end portion of the suture thread 2 inserted into the concave portion 13. In this case, as shown in FIG. 12A, the through-hole portion 13A passing through the crimp pieces 11 and 12 in the thickness direction may also be formed, instead of the concave portion 13. Thus, the large-diameter portion 2c is formed by the end portion of the suture thread 2 located outside the through-hole portion 13A and the crimp pieces 11 and 12.

Figure 13A:
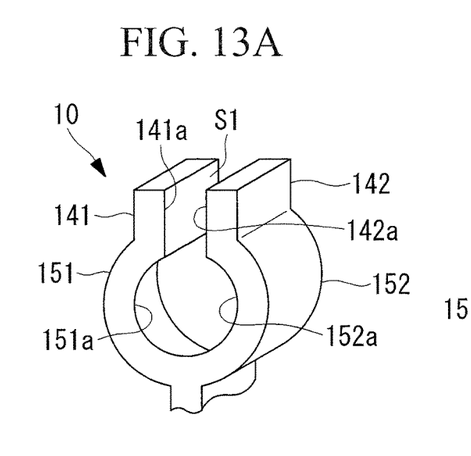
FIG. 13A is a perspective view showing still another modification of the first gripper and explaining the usage of the device.

The first gripper 10 shown in FIG. 13A includes almost-flat-shaped parallel sections (first sections) 141 and 142 that are disposed parallel to each other at the first side, and curve-shaped convex sections (second sections) 151 and 152 that project outward at the second side of the parallel sections 141 and 142. The parallel sections 141 and 142 function in the same way as the above-described crimp pieces 11 and 12 when inner faces 141a and 142a thereof are crimped together, and the convex sections 151 and 152 function in the same way as the above-described concave portions 13 when the end portion of the suture thread 2 is accommodated in an empty space formed by inner faces 151a and 152a thereof. Specifically, as shown in FIG. 13B, when the inner faces 141a and 142a are crimped together by crimping the parallel sections 141 and 142, the large-diameter portion 2c is formed by the end portion of the suture thread 2 accommodated inside the convex sections 151 and 152.

Figure 13B:
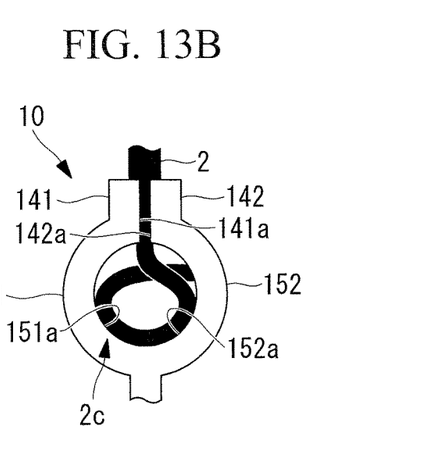
FIG. 13B is a front view of the first gripper shown in FIG. 13A.

Note that FIGS. 13A and 13B show the configuration of the first gripper 10 of this modification in which the convex sections 151 and 152 are formed in both piece members; however, the configuration of the first gripper 10 of this modification is not limited thereto. For example, the convex section 151 or 152 may be formed only in one of the pair of piece members. In this case, the shape of the convex section 151 or 152 is appropriately designed such that a space of sufficient size is ensured in the convex section 151 or 152 when the parallel sections 141 and 142 are crimped together.

Figure 14A:
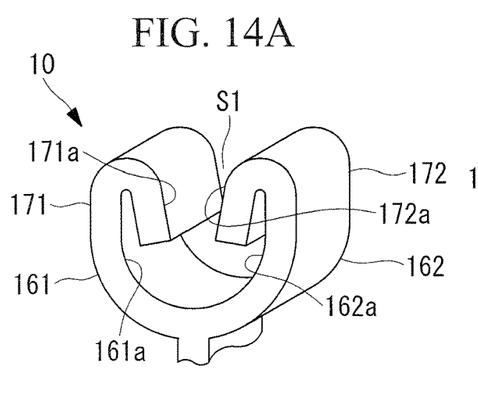
FIG. 14A is a perspective view showing still another modification of the first gripper.
Figure 14B:
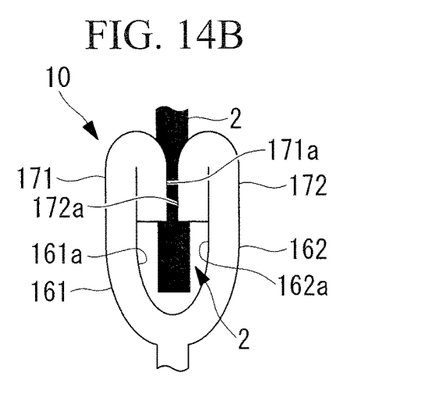
FIG. 14B is a front view of the first gripper shown in FIG. 14A.
Figure 15:
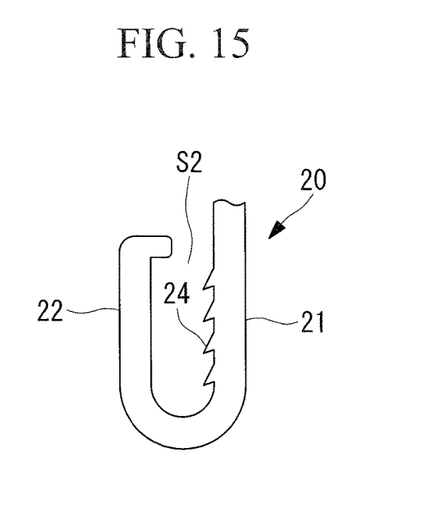
FIG. 15 is a front view showing a modification of the second gripper.

The first gripper 10 shown in FIG. 14A includes almost-flat-shaped parallel sections (accommodation portions) 161 and 162 that are disposed parallel to each other and hook-shaped sections (crimp pieces) 171 and 172 that are formed into a hook-like shape by bending end portions of the hook-shaped sections (crimp pieces) 171 and 172 inward at the first side of the parallel sections 161 and 162. The parallel sections 161 and 162 function in the same way as the above-described concave portions 13 when the end portion of the suture thread 2 is accommodated in the empty space formed between inner faces 161a and 162a thereof. The hook-shaped sections 171 and 172 function in the same way as the above-described crimp pieces 11 and 12 when inner faces 171a and 172a thereof are crimped together. Specifically, as shown in FIG. 14B, when the inner faces 171a and 172a are crimped together by crimping the hook-shaped sections 171 and 172, the large-diameter portion 2c is formed by the end portion of the suture thread 2 accommodated inside the parallel section 161 and 162.

Furthermore, in this embodiment, the pair of crimp pieces 11 and 12 of the first gripper 10 having a distance therebetween are opposed parallel to each other; however, the configuration of the crimp pieces 11 and 12 is not limited thereto. For example, the pair of crimp pieces 11 and 12 may be inclined so as to increase the size of the groove S1 from the second side toward the first side. This facilitates the insertion of the suture thread 2.

Figure 16:
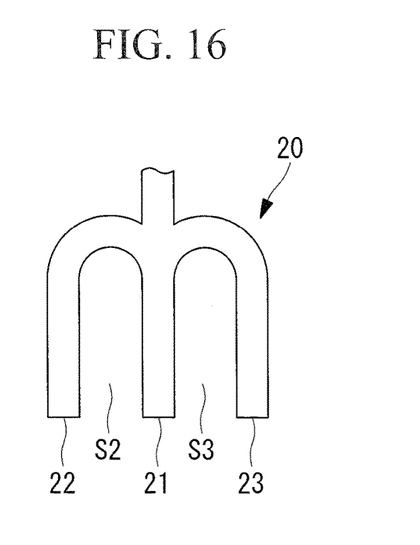
FIG. 16 is a front view showing another modification of the second gripper.
Figure 17:
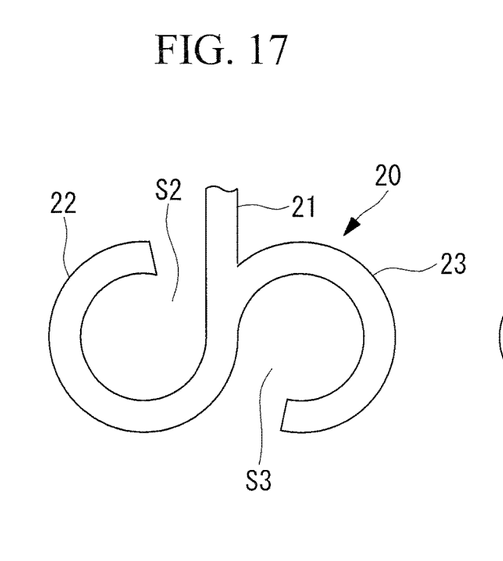
FIG. 17 is a front view showing still another modification of the second gripper.
Figure 18:
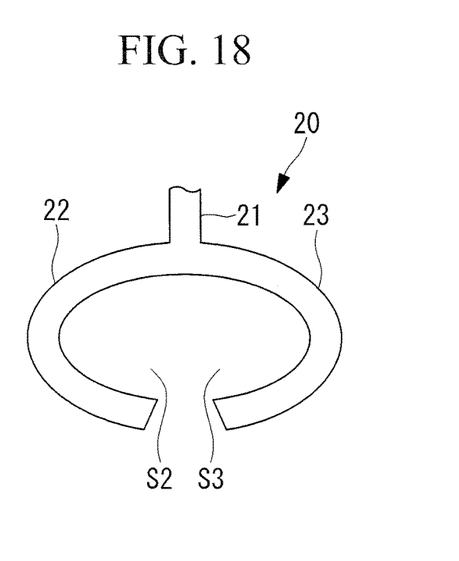
FIG. 18 is a front view showing still another modification of the second gripper.

Furthermore, in this embodiment, a description has been given of the anchor-shaped second gripper 20; however, the shape of the second gripper 20 is not limited thereto and can be appropriately modified. FIGS. 15 to 18 show modifications of the second gripper 20. The second gripper 20 shown in FIG. 15 has the single crimp piece 22. The shaft piece 21 or the crimp piece 22 may be provided with projections 24 that lock the suture thread 2 when the suture thread 2 is hooked thereon. The second gripper 20 shown in FIG. 16 is obtained by inverting the second gripper 20 shown in FIG. 1. The second gripper 20 shown in FIG. 17 is substantially S-shaped. The second gripper 20 shown in FIG. 18 is substantially C-shaped.

REFERENCE SIGNS LIST

1 ligation thread fastening tool
2 suture thread
3 suture needle
10 first gripper
11, 12 crimp pieces
11a, 12a inner faces
11b, 12b outer faces
13 concave portion (accommodation portion)
13A through-hole portion (accommodation portion)
141, 142 parallel sections (first sections, crimp pieces)
151, 152 convex sections (second sections, accommodation portions)
161, 162 parallel sections (second sections, accommodation portions)
171, 172 hook-shaped sections (first sections, crimp pieces)
20 second gripper
21 shaft piece
22, 23 crimp pieces
24 projections
100 ligation device
S1, S2, S3 grooves

The invention claimed is:

1. A ligation thread fastening tool comprising:
a first gripper that has a pair of first crimp pieces opposed to each other with a space therebetween and, when the first crimp pieces are crimped together, inner faces of the pair of crimp pieces in the space are opposed to each other and a first groove is disposed between the inner faces such that prior to the first crimp pieces being crimped together, a suture thread can be inserted into the first groove from a first side of the first crimp pieces toward a second side thereof; and
a second gripper that has a shaft piece that is connected to the first gripper, wherein
each inner face of the pair of first crimp pieces of the first gripper has an accommodation portion having a shape configured to accommodate an end portion of the suture thread inserted thereinto along the first groove, and
the second gripper has a second groove into which the suture thread can be inserted,
wherein the accommodation portion is formed of a concave portion that is formed in the inner face of each of the first crimp pieces, and
the concave portion is formed in a direction intersecting a direction of insertion of the suture thread;
wherein the second gripper comprises:
a third side;
a fourth side; and
a second crimp piece opposed to the shaft piece,
wherein the suture thread is inserted from the third side of the second crimp piece toward the fourth side of the second crimp piece,
the first groove is formed at the first side, and
the second groove is formed at the third side.

2. The ligation thread fastening tool according to claim 1, wherein the concave portion is formed in a direction intersecting a direction connecting the first side and the second side.

3. The ligation thread fastening tool according to claim 1, wherein the accommodation portion for each of the pair of first crimp pieces is disposed between first and second ends of the space.

4. The ligation thread fastening tool according to claim 3, wherein each accommodation portion is a concavity and the concavity is formed in a direction offset from a direction of insertion of the suture thread.

5. A ligation device comprising:
a suture thread; and
a ligation thread fastening tool according to one of claims 1 or 2, attached to one end portion of the suture thread,
wherein, the other end portion of the suture thread is inserted into the first groove;
the second gripper has a second crimp piece and a third crimp piece, each of which are opposed to the shaft piece;
the second groove is formed between an end face of the shaft piece and an inner face of the second crimp piece, and
the second crimp piece opens at a side of the first gripper.

6. The ligation device according to claim 5, further comprising a suture needle attached to the other end portion of the suture thread.

7. A ligation device comprising:
a suture thread; and
a ligation thread fastening tool according to claim 1, which is attached to one end portion of the suture thread;
wherein the one end portion of the suture thread is inserted from the first side into the first groove of the first gripper, and
the second groove opens at a side of the first side.

8. A ligation thread fastening tool comprising:
a first gripper that has a pair of first crimp pieces opposed to each other with a space therebetween and, when the first crimp pieces are crimped together, inner faces of the pair of crimp pieces in the space are opposed to each other and a first groove is disposed between the inner faces such that prior to the first crimp pieces being crimped together, a suture thread can be inserted into the first groove from a first side of the first crimp pieces toward a second side thereof; and
a second gripper that has a shaft piece that is connected to the first gripper, wherein
each inner face of the pair of first crimp pieces of the first gripper has an accommodation portion having a shape configured to accommodate an end portion of the suture thread inserted thereinto along the first groove, and
the second gripper has a second groove into which the suture thread can be inserted, wherein the accommodation portion is formed of a concave portion that is formed in the inner face of each of the first crimp pieces, and the concave portion is formed in a direction intersecting a direction of insertion of the suture thread;

wherein:

the second gripper has a third groove into which the suture thread can be inserted;

the second gripper has a second crimp piece and a third crimp piece each of which are opposed to the shaft piece;

the second groove is formed between a face of the shaft piece and an inner face of the second crimp piece, the third groove is formed between the face of the shaft piece and an inner face of the third crimp piece, and the shaft piece is interposed between the second crimp piece and the third crimp piece.

9. The ligation thread fastening tool according to claim 8, wherein the pair of the first crimp pieces and the second crimp piece each are disposed parallel to the shaft piece.

10. A ligation thread fastening tool comprising:

a first gripper that has a pair of first crimp pieces opposed to each other with a space therebetween and, when the first crimp pieces are crimped together, inner faces of the pair of crimp pieces in the space are opposed to each other and a first groove is disposed between the inner faces such that prior to the first crimp pieces being crimped together, a suture thread can be inserted into the first groove from a first side of the first crimp pieces toward a second side thereof; and a second gripper that has a shaft piece that is connected to the first gripper, wherein each inner face of the pair of first crimp pieces of the first gripper has an accommodation portion having a shape configured to accommodate an end portion of the suture thread inserted thereinto along the first groove, and the second gripper has a second groove into which the suture thread can be inserted, wherein the accommodation portion is formed of a concave portion that is formed in the inner face of each of the first crimp pieces, and the concave portion is formed in a direction intersecting a direction of insertion of the suture thread;

wherein the first side of the first gripper is opened and the second side, which is an opposite side from the first side, is closed, the second gripper has a second crimp piece and a third crimp piece each of which are opposed to the shaft piece;

the second groove is formed between a face of the shaft piece and an inner face of the second crimp piece, and is connected on the second side of the first gripper, and a first gripper side of the second gripper is opened and an opposite side of the second gripper is connected to the shaft piece.

* * * * *